United States Patent [19]

Yokokawa et al.

[11] Patent Number: 4,704,199
[45] Date of Patent: Nov. 3, 1987

[54] METHOD OF FORMING AN IRON OXIDE FILM BY REACTING SPUTTERING WITH CONTROL OF A GLOW DISCHARGE BY MONITORING AN EMISSION SPECTRUM OF IRON FROM THE GLOW DISCHARGE

[75] Inventors: Toshio Yokokawa; Yohichi Hirukawa, both of Tokyo, Japan

[73] Assignee: Anelva Corporation, Japan

[21] Appl. No.: 9,551

[22] Filed: Feb. 2, 1987

Related U.S. Application Data

[63] Continuation of Ser. No. 717,537, Mar. 29, 1985, abandoned.

[30] Foreign Application Priority Data

Mar. 30, 1984 [JP] Japan .................................. 59-62899

[51] Int. Cl.[4] ............................................. C23C 14/00
[52] U.S. Cl. ............................. 204/298; 204/192.12; 204/192.15; 204/192.2
[58] Field of Search ................ 204/298, 192.2, 192.15, 204/192.12

[56] References Cited

U.S. PATENT DOCUMENTS

| | | | |
|---|---|---|---|
| 4,036,167 | 7/1977 | Lu | 204/298 |
| 4,394,237 | 7/1983 | Donnelly et al. | 204/298 |
| 4,407,709 | 10/1983 | Enjouji et al. | 204/298 |
| 4,491,499 | 1/1985 | Jerde et al. | 204/298 |

OTHER PUBLICATIONS

Chen et al, IBM Tech. Disc. Bull., 22 (1980), p. 5431.
Schiller et al., Thin Solid Films, 96 (1982), pp. 235–240.
Greene (I) J. Vac. Sci. Tech., 15 (1978), pp. 1716–1729.
Steinbruchel, J. Vac. Sci. Tech., 16 (1979), pp. 251–254.
Enjouji et al., Thin Solid Films, 108 (1983), pp. 1–7.
Greene, J. Vac. Sci. Tech., 15 (1978), pp. 1–2.
Greene et al., J. Vac. Sci. Tech., 10 (1973), pp. 1144–1149.
Chem. Abstracts, 98, #136473.

*Primary Examiner*—Arthur P. Demers
*Attorney, Agent, or Firm*—Laff, Whitesel, Conte & Saret

[57] ABSTRACT

In a method of forming an iron oxide film of either $Fe_3O_4$ or $\alpha\text{-}Fe_2O_3$ on a substrate with reactive sputtering of a target of iron, intensity of an emission spectrum of iron is previously determined as a predetermined value in connection with a desired one of $Fe_3O_4$ and $\alpha\text{-}Fe_2O_3$ films. A light beam emitted from the glow discharge is measured to produce an electric signal representative of intensity of a measured spectrum of iron. Control operation is carried out to adjust the measured spectrum to the predetermined value. The electric signal may control either a flow rate of introducing oxygen gas into the space or intensity of an electric field produced between the substrate and the target.

14 Claims, 5 Drawing Figures

METHOD OF FORMING AN IRON OXIDE FILM BY REACTING SPUTTERING WITH CONTROL OF A GLOW DISCHARGE BY MONITORING AN EMISSION SPECTRUM OF IRON FROM THE GLOW DISCHARGE

This application is a continuation, of application Ser. No. 6,717,537, filed Mar. 29, 1985, now abandoned.

BACKGROUND OF THE INVENTION

This invention relates to a method of forming an iron oxide film of, for example, $\alpha\text{-}Fe_2O_3$ or $Fe_3O_4$, which is necessary to form a magnetic recording medium having high packing or recording density for use in a magnetic disk. This invention relates also to a sputtering device for use in carrying out the method.

In order to achieve high packing density in the magnetic disk, it is preferable that a magnetic recording medium has a thin thickness. As such a magnetic recording medium, a recent attention is directed towards a thin film of $\gamma\text{-}Fe_2O_3$. Two conventional methods of forming a $\gamma\text{-}Fe_2O_3$ film will be described in the following.

In a first method of forming the thin film of $\gamma\text{-}Fe_2O_3$, an $\gamma\text{-}Fe_2O_3$ film is formed by reactive sputtering at first. Thereafter, the $\gamma\text{-}Fe_2O_3$ film is transformed into an $Fe_3O_4$ film by first heat treatment and subsequently into the $\gamma\text{-}Fe_2O_3$ by second heat treatment. The second heat treatment may be called a gamma transformation process, namely, a $\gamma$-izing process.

In a second method of forming the thin film of $65\text{-}Fe_2O_3$, an $Fe_3O_4$ film is directly deposited by reactive sputtering and is thereafter transformed into the $\gamma\text{-}Fe_2O_3$ film by the gamma transformation process.

The second method has a tendency that a phase of iron or $\alpha\text{-}Fe_2O_3$ is mixed with the thin film of $Fe_3O_4$ during the reactive sputtering. This disables to effectively carry out the gamma transformation process. In this view, it is necessary to stably form the film consisting of a single phase of $Fe_3O_4$.

It is important to establish a method of stably forming the thin film of $\alpha\text{-}Fe_2O_3$ and the thin film of $Fe_3O_4$ in order to achieve mass production of the magnetic recording medium and to thereby manufacture the magnetic recording medium at a low cost.

In a conventional method of forming an iron oxide film of $\alpha\text{-}Fe_2O_3$ or $Fe_3O_4$ on a substrate by reactive sputtering, the substrate is located in a space in face to face relation to a target disposed in the space. The target consists essentially of iron. An introducing gas which is introduced into the space consists either essentially of oxygen or a combination of argon and oxygen. An electric field is produced between the target and the substrate to generate a glow discharge in the space. An electric voltage source is connected between the target and the substrate to produce the electric field. Sputtering of the target is carried out by the aid of the glow discharge. As a result, the iron oxide film is formed on the substrate.

In the conventional method, reactive sputtering is carried out by controlling a voltage which is applied to the target by the electric voltage source, a pressure of the space, and a duration of sputtering so that the voltage, the pressure, and the duration are adjusted to respective preselected values. The pressure must generally be measured far from a region where the glow discharge is generated. It is therefore difficult to measure a true partial pressure of oxygen in the region. In addition, the most suitable condition of the partial pressure of oxygen complicatedly varies by the degree of reaction of a surface of the target and a rate of forming the iron oxide film. On account of the above-mentioned reasons, it is difficult to control the state of the glow discharge at a constant state. It is therefore impossible to stably form the iron oxide film of $\alpha\text{-}Fe_2O_3$ or $Fe_3O_4$.

In each of Japanese Patent Publications Nos. 32716/1979, 14058/1980, and 14059/1980, an improved method for stably forming an iron oxide film of $Fe_3O_4$ is disclosed wherein sputtering is carried out by accurately controlling the voltage applied to the target. Accurate control of the voltage is carried out so as to maintain a preferred glow discharge. As will later be described with reference to one of several figures of the accompanying drawing, the improved method needs a shutter which is disposed between the target and the substrate. The shutter acts to restrict formation of the iron oxide film to a part of a surface of the substrate. The substrate is rotated so that the iron oxide film can be formed on a whole surface of the substrate. However, use of the shutter inevitably makes the reactive sputtering long so as to obtain a predetermined thickness of the iron oxide film. In addition, such a long sputtering results in an increase of useless consumption of the target and makes it difficult to form the iron oxide film at a low cost.

SUMMARY OF THE INVENTION

It is therefore an object of this invention to provide a method capable of stably forming an iron oxide film.

It is another object of this invention to provide a method of forming an iron oxide film of the type described, which is capable of quickly obtaining a predetermined thickness of the iron oxide film.

It is still another object of this invention to provide a method of forming an iron oxide film of the type described, which is capable of forming the iron oxide film at a low cost.

Other objects of this invention will become clear as the description proceeds.

A method to which this invention is applicable is for forming an iron oxide film on a substrate. The method includes the steps of locating the substrate in an evacuative space in face to face relation to a target which is disposed in the evacuative space and which consists essentially of iron, evacuating the evacuative space to provide an evacuated space, introducing a mixture of inert gas and oxygen gas into the evacuated space at a rate to provide a gas filled space, and producing an electric field of a strength between the target and the substrate to generate a glow discharge in the gas filled space thereby to carry out sputtering of the target and to form the iron oxide film on the substrate. According to this invention, the method comprises the steps of monitoring a light beam emitted from the glow discharge to produce an electric signal which is related to intensity of an emission spectrum of iron, and controlling at least one of the rate of introducing the mixture into the evacuated space and the strength of the electric field to adjust the electric signal to a predetermined value.

DESCRIPTION OF THE PREFERRED EMBODIMENTS

Figure 1:
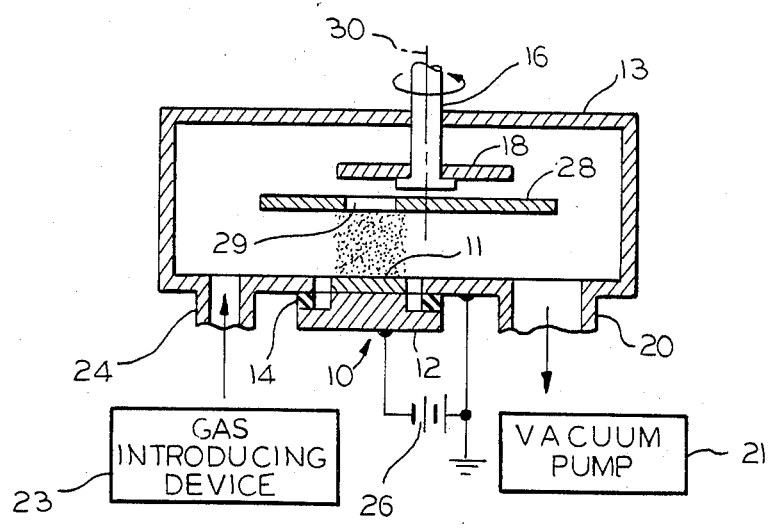
FIG. 1 is a schematic vertical sectional view of a sputtering device which is for use in carrying out a conventional method of forming an iron oxide film.

Referring to FIG. 1, a conventional method will be described for a better understanding of this invention. The conventional method is substantially equivalent to the method which is disclosed in each of Japanese Patent Publications Nos. 32716/1979, 14058/1980, and 14059/1980 and which is briefly described in the preamble of the instant specification. The conventional method is for stably forming an iron oxide film of $Fe_3O_4$. A sputtering device for use in carrying out the conventional method comprises a target member 10. The target member 10 comprises a target 11 consisting essentially of iron and a conductive body 12 in contact with the target 11. The target member 10 is attached to an attachment opening of a chamber 13 of a conductive material by means of an electrical insulator 14. On attaching the target member 10 to the attachment opening, the target 11 is located so as to be exposed to a hollow space defined in the chamber 13. A holder 16 is rotatably supported through a supporting opening of the chamber 13. The holder 16 is for holding a substrate 18 in face to face relation to the target 11 with a predetermined or evacuative space left between the target 11 and the substrate 18.

Together with the predetermined space, the hollow space can be evacuated through a pipe 20 by a vacuum pump 21. A gas introducing device 23 is for introducing a mixture of inert gas, such as argon, and oxygen gas into the hollow space through a pipe 24.

A d.c. power source 26 is for supplying a d.c. voltage between the target member 10 and the chamber 13. The chamber 13 is grounded. The target member 10 is kept at a negative electric potential by the d.c. power source 26. The d.c. voltage produces an electric field between the target 11 and the substrate 18 to generate a glow discharge in the predetermined space. Therefore, the d.c. power source 26 may be referred to as an electric field producing device.

A shutter 28 is disposed between the target 11 and the substrate 18. The shutter 28 is grounded through the chamber 13. The shutter 28 has an opening 29 to restrict formation of the iron oxide film to a part of lower surface of the substrate 18.

On forming the iron oxide film of $Fe_3O_4$ on the substrate 18 by the use of the sputtering device, the hollow space is evacuated by the vacuum pump 21 to provide an evacuated space. The mixture of inert gas and oxygen gas is introduced into the evacuated space by the gas introducing device 23 to provide a gas filled space. The electric field is produced between the target 11 and the substrate 18 by the d.c. power source 26 to generate the glow discharge in the gas filled space. Sputtering of the target 11 is carried out by the glow discharge.

In order to stably form the iron oxide film of $Fe_3O_4$, the sputtering is carried out by accurately controlling the voltage supplied to the target 11 in the conventional method as described in the preamble of the instant specification. Accurate control is made so as to maintain a preferred glow discharge. Particles sputtered from the target 11 are deposited on the substrate 18 through the opening 29 of the shutter 28 to form the iron oxide film of $Fe_3O_4$ on a part of the surface of the substrate 18. In order to uniformly form the iron oxide film on a whole surface of the substrate 18, the substrate 18 is rotated around a center axis 30 of the holder 16 during the sputtering. Rotation of the substrate 18 is carried out by a driving device (not shown) so that the holder 16 is rotated around the center axis 30 in a direction indicated by an arrow depicted in FIG. 1. If the substrate 18 is heated to a suitable temperature, it is expected that reaction and crystallization of the already formed iron oxide film favorably proceed during time intervals in which formation of the iron oxide film is disabled by the shutter 28.

However, the conventional method has defects which result from the presence of the shutter 28. That is, it needs much time to obtain a predetermined thickness of the film of $Fe_3O_4$. It is therefore incapable of quickly obtaining the predetermined thickness of the film of $Fe_3O_4$. Moreover, the material of the target 11 is uselessly spent because a considerable quantity of sputtered particles is prohibited by the shutter 28 from reaching the substrate 18 and forms a deposit of an iron oxide onto the shutter 28. Therefore, the conventional method is incapable of forming the iron oxide film of $Fe_3O_4$ at a low cost. In addition, the shutter 28 should often be cleaned to remove the deposit on the shutter 28. This is because fragments of the deposit peel off the shutter 28 to give rise to unusual discharge and pinholes of the iron oxide film of $Fe_3O_4$ when the deposit becomes thick on the shutter 28.

This invention is for removing the defect and provides a method of forming an iron oxide film of, for example, $\alpha\text{-}Fe_2O_3$ or $Fe_3O_4$ by reactive sputtering in the presence of a glow discharge, wherein the glow discharge is controlled by monitoring an emission spectrum of iron emitted from the glow discharge.

In this invention, it has been found out that formation of the iron oxide film is detected by monitoring an emission spectrum of iron. Although description is made about a method of monitoring emission spectra of aluminum, chromium, and an alloy of indium and tin in Japanese Patent Application No. 113685/1982 assigned to ANELVA CORPORATION, no application of the method is considered to transformation of iron.

Figure 2:
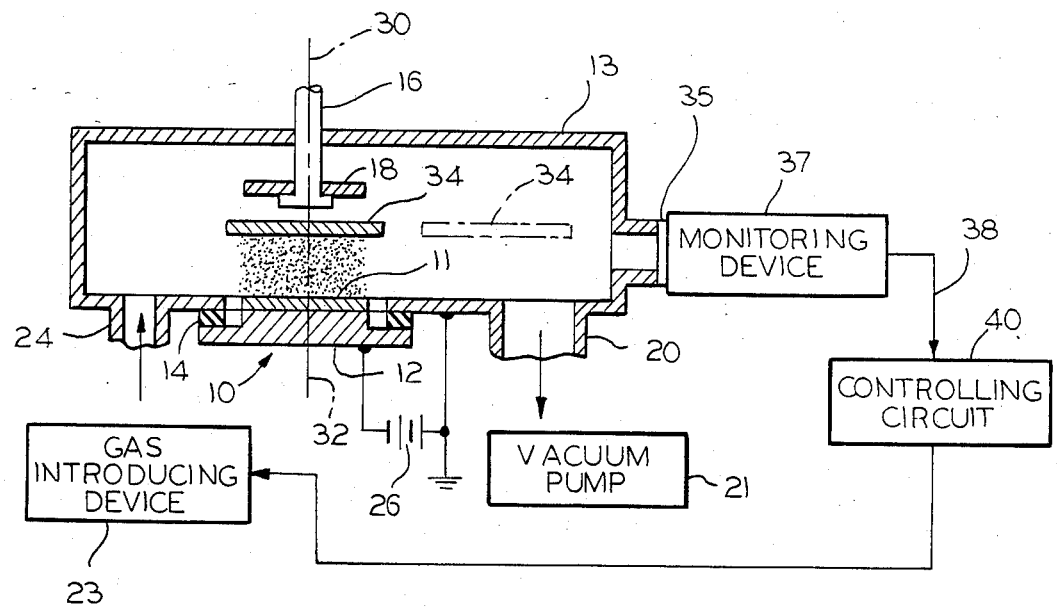
FIG. 2 is a schematic vertical sectional view of a sputtering device which is for use in carrying out methods according to first and second embodiments of this invention.

Referring to FIG. 2, a sputtering device will now be described which is for use in carrying out this invention. The sputtering device is for stably forming an iron oxide film of either $\alpha\text{-}Fe_2O_3$ or $Fe_3O_4$ by monitoring the emission spectrum of iron in a manner to be described. The sputtering device comprises similar parts designated by like reference numerals. The target 11 is of a circular plate which consists of iron and which has an upper planar surface to be sputtered. The target 11 has a center axis 32 perpendicular to the upper planar surface. The target 11 is fixed to the conductive body 12 in the manner known in the art. The substrate 18 is of a circular plate having a lower planar surface on which the iron oxide film is to be formed. The substrate 18 has a center axis perpendicular to the lower planar surface. The substrate 18 has a circular hole in a central position thereof. The circular hole is extended along the center axis of the substrate 18. The holder 16 is of a cylinder rod extended along the center axis 30 of the holder 16. The cylinder rod has a flange perpendicularly of the center axis 30 at a lower end thereof. The substrate 18 is held by the flange with the cylinder rod inserted into the circular hole. The center axis of the substrate 18 is coincident with the center axis 32 of the target 11. The lower planar surface of the substrate 18 is parallel to the upper planar surface of the target 11. A movable shutter 34 is positioned between the substrate 18 and the target 11. The shutter 34 is grounded through the chamber 13. The shutter 34 is movable between a first position depicted by a solid line and a second position depicted by a dash-dot line in a direction perpendicular to the center axis 30. When placed in the first position, the shutter 34 prevents formation of the iron oxide film on the substrate 18. When moved to the second position, the shutter 34 enables to form the iron oxide film on the substrate 18.

A glass plate 35 is attached to an opening of the chamber 13. A light beam emitted from a glow discharge passes through the glass plate 35. A monitoring device 37 is attached to an outer surface of the glass plate 35. The monitoring device 37 is for monitoring the light beam passed through the glass plate 35 to produce an electric signal 38 which is related to intensity of an emission spectrum of iron. The monitoring device 37 measures the intensity of the emission spectrum of iron and intensity of an emission spectrum of argon used as the inert gas. The monitoring device 37 produces the electric signal 38 which represents either the intensity of the emission spectrum of iron or a ratio of the intensity of the emission spectrum of iron to the intensity of the emission spectrum of argon. A controlling circuit 40 is coupled to the gas introducing device 23. Responsive to the electric signal 38, the controlling circuit 40 controls the gas introducing device 23 to adjust the electric signal 38 to a predetermined value. More particularly, the controlling circuit 40 controls a partial flow rate of introducing the oxygen gas into the hollow space so that the electric signal 38 becomes equal to the predetermined value.

On forming the iron oxide film of $Fe_3O_4$ or $\alpha-Fe_2O_3$ on the substrate by the use of the sputtering device, the hollow space is evacuated by the vacuum pump 21 to provide an evacuated space. The evacuated space is kept at a pressure of about $10^{-6}$ Torr. Inert gas of argon is introduced into the evacuated space at a predetermined flow rate by the gas introducing device 23 to provide a gas filled space. Oxygen gas is also introduced into the gas filled space at a provisional flow rate by the gas introducing device 23. An electric field is produced between the target 11 and the shutter 34 positioned in the first position by the d.c. power source 26 to generate the glow discharge in the gas filled space. Presputtering of the target 11 is carried out by the glow discharge.

Simultaneously, the monitoring device 37 and the controlling circuit 40 are operated in order to start automatic control of the partial flow rate of introducing the oxygen gas. The controlling circuit 40 controls the partial flow rate to adjust the electric signal 38 to the predetermined value. The presputtering is carried out for a predetermined duration so as to clean the upper surface of the target 11. When the predetermined duration goes by, a transfer mechanism (not shown) is operated. The transfer mechanism transfers the shutter 34 from the first position to the second position. As a result, formation of the iron oxide film is started on the substrate 18 and lasts for a preselected duration until a predetermined thickness of the iron oxide film is obtained. After lapse of the preselected duration, supply of the d.c. voltage to the target 11 is stopped to finish the formation of the oxide film.

Figure 3:
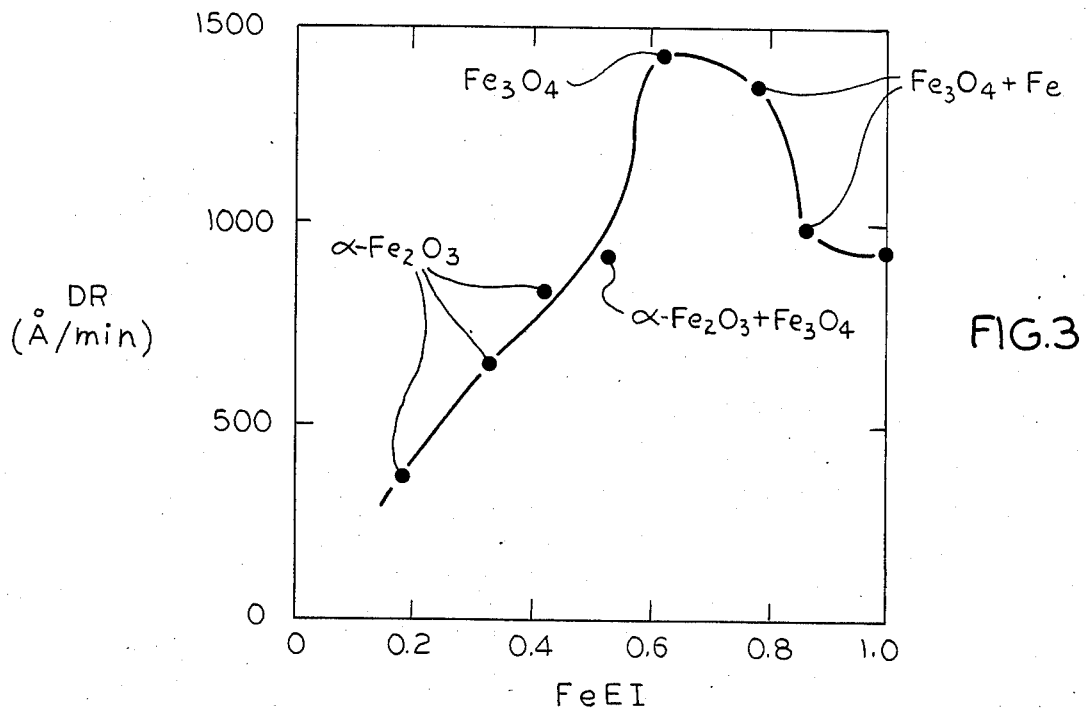
FIG. 3 shows a graph for use in describing the method according to the first embodiment of this invention.

Referring to FIG. 3 afresh and FIG. 2 again, a method according to a first embodiment of this invention will now be described. The method is for forming an iron oxide film of $Fe_3O_4$ or $\alpha-Fe_2O_3$. In the method, the monitoring device 37 measures the intensity of the emission spectrum of iron. The emission spectrum of iron appears at a wavelength of, for example, about 371 nanometers. The monitoring device 37 produces the electric signal 38 representative of the intensity of the emission spectrum of iron. The controlling circuit 40 controls the partial flow rate of introducing the oxygen gas into the chamber 13 to adjust the electric signal 38 to a predetermined value.

Operation of the controlling circuit 40 will now be described in detail. Examination is at first made about various crystal structures of iron oxide films by the use of the sputtering device illustrated in FIG. 2 so as to detect a relationship between the crystal structures of the iron oxide film and the emission spectrum of iron. A result of the examination is shown in FIG. 3. The oxide films are formed on the substrate 18 of glass in an environment consisting of a combination of argon and oxygen with an electric current due to the glow discharge maintained at a constant value. The crystal structures of the oxide film are observed by the use of an X-ray diffraction device in which a $CuK\alpha$ line is caused to be incident on the oxide films. In FIG. 3, the ordinate represents a deposition rate DR of depositing or forming the oxide film while the abscissa represents physical quantity related to intensity of the emission spectrum of iron on sputtering. The physical quantity is specified by a relative intensity determined in a manner mentioned below. The intensity of the emission spectrum of iron is measured during reactive sputtering carried out in a first environment consisting of a combination of argon and oxygen and may be called a first value. A reference intensity of the emission spectrum of iron is measured during sputtering carried out in a second environment which does not include oxygen gas but consists only of argon gas. The reference intensity of the emission spectrum of iron may be referred to as a second value. The abscissa represents the relative intensity, namely, a ratio FeEI of the first value to the second value. That is, the ratio FeEI is equal to unity in the case of the second environment.

It is apparent from FIG. 3 that the iron oxide film of $Fe_3O_4$ is deposited by controlling the flow rate of introducing the oxygen gas. For this purpose, the controlling circuit 40 is adjusted in the second environment. The electric signal 38 provides a reference value in the second environment and the controlling circuit 40 controls the gas introducing device 23 with reference to the reference value of the electric signal 38. The controlling circuit 40 controls the gas introducing device 23 in relation to the reference value in the first environment so as to adjust the electric signal 38 to the predetermined value determined by the iron oxide film to be formed.

In order to realize the relative intensity of 0.62, the predetermined value is selected to a value obtained by multiplying the reference value by 0.62 when formation of the $Fe_3O_4$ film is carried out.

On the other hand, formation of iron oxide film consisting of $\alpha\text{-}Fe_2O_3$ is achieved by controlling the flow rate of introducing the oxygen gas so that the relative intensity falls within a range between 0.2 and 0.42. The predetermined value of the controlling circuit 40 is selected to a value obtained by multiplying the reference value by a value between 0.2 and 0.42.

In order to form or deposit an iron oxide film consisting of a compound of $Fe_3O_4$ and $\alpha\text{-}Fe_2O_3$, the flow rate of introducing the oxygen gas may be controlled so that the relative intensity becomes equal to a range between 0.5 and 0.6. The predetermined value of the controlling circuit 40 is selected to a value obtained by multiplying the reference value by a value between 0.5 and 0.6.

As mentioned above, the flow rate of introducing the oxygen gas into the chamber 13 is controlled in order to maintain the relative intensity constant during sputtering.

It is assumed that the state of the glow discharge changes during sputtering. This causes changes of the degree of oxidation of the surface of the target 11 and the rate of forming the oxide film. However, such changes cause the amount of iron atom produced by sputtering of the target 11 to change. This appears as a change of the intensity of the emission spectrum of iron measured by the monitoring device 37. The change of intensity mentioned above results in a variation of the electric signal 38 produced from the monitoring device 37. The controlling circuit 40 controls the flow rate of introducing the oxygen gas so as to remove the variation of the electric signal 38 and to thereby render the electric signal 38 equal to the predetermined value. As a result, it is possible to maintain the glow discharge at a constant state. This makes it possible to continuously form the iron oxide film having a predetermined crystal structure and a predetermined composition.

The above-mentioned method according to the first embodiment of this invention may be unsuitable to form the iron oxide film for a long time. This is because measurement of true intensity of the emission spectrum of iron becomes difficult in the monitoring device 37 as an iron oxide film is inevitably formed on an inner surface of the glass plate 35 for a long sputtering time.

Figure 4:
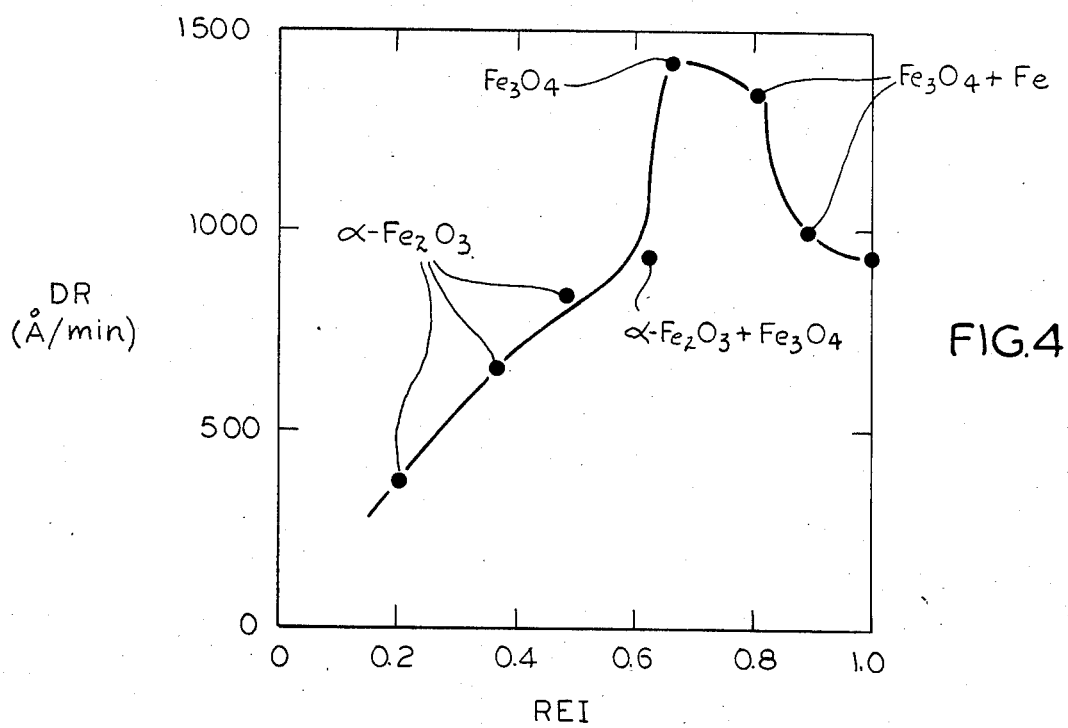
FIG. 4 shows a graph for use in describing the method according to a second embodiment of this invention.

Referring to FIG. 4 afresh and FIG. 2 again, a method according to the second embodiment of this invention is to remove the above-mentioned defect and will now be described. The method is for forming an iron oxide film of $Fe_3O_4$ or $\alpha\text{-}Fe_2O_3$. In the method, the monitoring device 37 measures not only the intensity of the emission spectrum of iron but also intensity of an emission spectrum of argon as the inert gas. The emission spectrum of argon appears at a wavelength of, for example, about 420 nanometers though the emission spectrum of iron appears at a wavelength of, for example, about 371 nanometers. The monitoring device 37 produces the electric signal 38 representative of a ratio of the intensity of the emission spectrum of iron to the intensity of the emission spectrum of argon. The controlling circuit 40 controls the partial flow rate of introducing the oxygen gas into the chamber 13 to adjust the electric signal 38 to a predetermined value.

Operation of the controlling circuit 40 will now be described in detail. Examination is at first made about various crystal structures of iron oxide films by the use of the sputtering device illustrated in FIG. 2 as is the case with the first embodiment of this invention. A result of the examination is shown in FIG. 4. In FIG. 4, the ordinate represents a deposition rate DR of depositing or forming the oxide film while the abscissa represents physical quantity related to a ratio of the intensity of the emission spectrum of iron to the intensity of the emission spectrum of argon on sputtering. The physical quantity is specified by a relative ratio determined in a manner mentioned below. The ratio of the intensity of the emission spectrum of iron to the intensity of the emission specrum of argon is measured during reactive sputtering carried out in a first environment consisting of a combination of argon and oxygen and may be called a first ratio. A reference ratio of the intensity of the emission spectrum of iron to the intensity of the emission spectrum of argon is measured during sputtering carried out in a second environment which does not include oxygen gas but consists only of argon gas. The reference ratio may be referred to as a second ratio. The abscissa represents the relative ratio, namely, a ratio REI of the first ratio to the second ratio. That is, the ratio REI is equal to unity in the case of the second environment.

It is apparent from FIG. 4 that an iron oxide film of $Fe_3O_4$ is deposited by controlling the flow rate of introducing the oxygen gas so that the relative ratio becomes equal to a value obtained by multiplying the second ratio by 0.67.

The electric signal 38 provides a reference value in the second environment as is the case with the first embodiment. In order to realize the relative ratio of 0.67, the predetermined value of the controlling circuit 40 is selected to a value obtained by multiplying the reference value by 0.67 when formation of the $Fe_3O_4$ film is carried out.

Like the relative value described in conjunction with FIG. 3, the relative ratio is determined by multiplying the second ratio by a value between 0.2 and 0.49. To this end, the flow rate of introducing the oxygen gas is controlled to form an iron oxide film of $\alpha\text{-}Fe_2O_3$.

In order to form or deposit an iron oxide film of a compound of $Fe_3O_4$ and $65\text{ -}Fe_2O_3$, the flow rate of introducing the oxygen gas may be controlled so that the relative ratio becomes equal to a range between 0.5 and 0.6.

The intensities of the emission spectra of iron and argon are individually measured in the above-mentioned method. Measured intensities of the emission spectra of iron and argon may equally be attenuated when an undesired iron oxide film is formed on the inner surface of the glass plate 35. However, a ratio of the measured intensities remains unchanged. Inasmuch as the ratio of the measured intensities can be observed in this embodiment, it is possible to continuously form the iron oxide film of a desired crystal structure for a long time.

Figure 5:
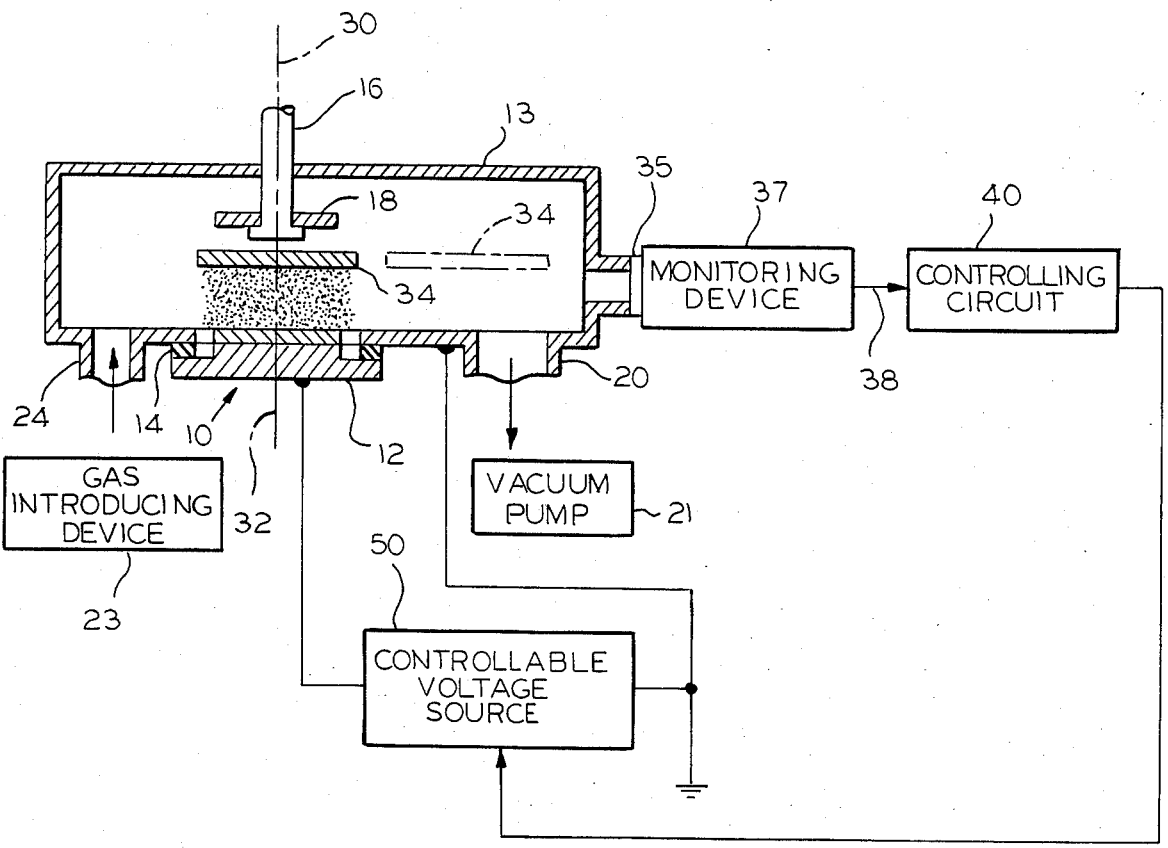
FIG. 5 is a schematic vertical sectional view of a sputtering device which is for use in carrying out a method according to a third embodiment of this invention.

Referring to FIG. 5, a method according to a third embodiment of this invention will now be described. The method is for stably forming an iron oxide film of, for example, $Fe_3O_4$ or $\alpha\text{-}Fe_2O_3$. The method is carried out by the use of a sputtering device similar to that illustrated in FIG. 2 except that a controllable voltage source 50 is operable as the electric field producing device and is controlled by a control signal supplied from the controlling circuit 40 and that the gas introducing device 23 introduces a mixture of inert gas, such as argon, and oxygen gas into the chamber 13 at a controllable flow rate. More specifically, the controllable voltage source 50 is coupled to the controlling circuit 40 and to the conductive body 12. Supplied with the control signal from the controlling circuit 40, the controllable voltage source 50 produces a negative voltage. As a result, the strength of the electric field is controlled in accordance with the negative voltage to adjust the electric signal 38 to the predetermined value. In other words, the controlling circuit 40 controls the strength of the electric field to adjust the electric signal to the predetermined value. With this method, the iron oxide film is stably deposited by controlling the strength of the electric field, like in the methods described in conjunction with FIGS. 2 through 4.

As mentioned before, the method according to this invention serves to neatly deposit the iron oxide film selected from a group of $Fe_3O_4$, $60$-$Fe_2O_3$, and a compound of $Fe_3O_4$ and $\alpha$-$Fe_2O_3$. A shutter 28 (in FIG. 1) is unnecessary in this method. Therefore, the method is capable of quickly depositing the iron oxide film to a desired thickness. This enables effective use of the target 11 and renders the iron oxide film cheap. In addition, the method facilitates maintainance of the sputtering device because no cleaning of the shutter 28 (FIG. 1) is necessary. Moreover, the method makes use of the relationship between the intensity of the emission spectrum of iron and the crystal structures of the oxide film. The relationship has high universality. It is readily possible to render the intensity of the emission spectrum of iron equal to a predetermined value. The method can therefore readily be carried out. Inasmuch as the predetermined value can readily be determined with reference to FIGS. 3 and 4, actual sputtering condition can be readily selected in consideration of the predetermined value.

While the present invention has thus far been described in conjunction with several preferred embodiments thereof, it will now be readily possible for those skilled in the art to practice this invention in various other manners. For example, a controllable electric power source which supplies the target 11 with an a.c. voltage of, for example, a high frequency may be used instead of the controllable voltage source 50. In this case, an output signal of the controllable electric power source is controlled by the control signal from the controlling circuit 40 in any one of power, frequency, and waveform thereof. The object 18 may be rotated in order to achieve uniformity of the iron oxide film on the substrate 18. The inert gas may be of, for example, neon, krypton, or xenon. The target 11 may be an alloy of iron and a small amount of additive of, for example, cobalt.

What is claimed is:

1. A method forming an iron oxide film on a substrate, said method including the steps of locating said substrate in an evacuative space and in a face-to-face relationship with respect to a target which is disposed in said evacuative space and which substantially comprises iron; evacuating said evacuative space; introducing a mixture of inert gas and oxygen gas into said evacuated space at a gas flow rate which provides a gas filled space; and producing an electric field having a strength between said target and said substrate to generate a glow discharge in said gas filled space whereby sputtering said target and forming said iron oxide film on said substrate, wherein the improvement comprises the steps of:
    selecting a factor which is related to an intensity of an emission spectrum of said iron and which is variable to specify a species of said iron oxide film, said factor being a ratio between said intensity of the emission spectrum of said iron and an intensity of an emission spectrum of the inert gas, said ratio being dependent on said gas flow rate and said species of the iron film that is used;
    monitoring said factor by observing a light beam emitted from said glow discharge to produce an electric signal which is representative of said factor; and
    controlling at least one of said gas flow rate and said strength of the electric field to adjust said factor to a desired value which is determined in relationship to said species of the iron oxide film.

2. A method as claimed in claim 1, wherein said iron oxide film consists of $Fe_3O_4$.

3. A method as claimed in claim 1, wherein said iron oxide film consists of $\alpha$-$Fe_2O_3$.

4. A method as claimed in claim 1, wherein said iron oxide film consists of $Fe_3O_4$ and $\alpha$-$Fe_2O_3$.

5. The method as claimed in claim 1, wherein said factor is that intensity of the emission spectrum of said iron which depends on said gas rate and which can specify said species of the iron oxide film.

6. The method as claimed in claim 5, wherein said oxygen gas is controlled in said controlling step to adjust said intensity of the emission spectrum of the iron to said desired value.

7. A method as claimed in claim 1, wherein said oxygen gas is controlled in said controlling step to adjust said ratio to said desired value.

8. A sputtering device comprising a target substantially comprising iron, holding means for holding a substrate in a face-to-face relationship with said target, a space being left between said target and said substrate, gas introducing means for introducing a mixture of inert gas and oxygen gas into said space at a gas flow rate, and electric field producing means for producing an electric field between said target and said substrate to generate a glow discharge in said space, said sputtering device sputtering said target in the presence of said glow discharge to form an iron oxide film on said substrate, the improvement wherein:
    a factor is selected in relationship to an intensity of an emission spectrum of said iron, said factor being variable to correspond to a species of said iron oxide film, said factor being a ratio beteen said intensity of an emission spectrum of said iron and an intensity of an emission spectrum of the inert gas, said ratio being dependent on said gas flow rate and on the species of the iron oxide film that is used;
    said sputtering device comprising;
    monitoring means for monitoring said factor in response to a light beam emitted from said glow discharge to produce an electric signal which is representative of said factor; and
    controlling means coupled to at least one of said gas introducing means and said electric field producing means and being responsive to said electric signal for controlling said at least one of the gas introducing means and the electric field producing means to adjust said factor to a desired value which is determined in relationship to said species of the iron oxide film.

9. A sputtering device as claimed in claim 8, wherein said iron oxide film consists of $Fe_3O_4$.

10. A sputtering device as claimed in claim 8, wherein said iron oxide film consists of $\alpha$-$Fe_2O_3$.

11. A sputtering device as claimed in claim 8, wherein said iron oxide film consists of $Fe_3O_4$ and $\alpha\text{-}Fe_2O_3$.

12. The sputtering device as claimed in claim 8, wherein said factor is that intensity of the emission spectrum of said iron which depends on said gas flow rate and which specifies said species of the iron oxide film.

13. The sputtering device as claimed in claim 12, wherein said oxygen gas is controlled by said controlling means to adjust said intensity of the emission spectrum of the iron to said desired value.

14. The sputtering device as claimed in claim 8, wherein said oxygen gas is controlled by said controlling means to adjust said ratio to said desired value.

* * * * *